United States Patent [19]

Lund

[11] Patent Number: 5,431,908
[45] Date of Patent: Jul. 11, 1995

[54] METHOD FOR PREPARING POLYHALIDE RESIN DISINFECTANTS

[75] Inventor: James L. Lund, Lake Elmo, Minn.

[73] Assignee: Recovery Engineering, Inc., Minneapolis, Minn.

[21] Appl. No.: 32,620

[22] Filed: Mar. 17, 1993

[51] Int. Cl.$^6$ .............................................. A61K 31/74
[52] U.S. Cl. ..................... 424/78.1; 424/78.26
[58] Field of Search ............... 424/78.26, 405, 28.1

[56] References Cited

U.S. PATENT DOCUMENTS

| | | |
|---|---|---|
| 3,316,173 | 4/1967 | Mills et al. |
| 3,462,363 | 8/1969 | Mills |
| 3,817,860 | 6/1975 | Lambert et al. |
| 3,923,665 | 12/1975 | Lambert et al. |
| 4,076,622 | 2/1978 | Costin |
| 4,187,183 | 2/1980 | Hatch |
| 4,190,529 | 2/1980 | Hatch |
| 4,238,477 | 12/1980 | Lambert |
| 4,594,392 | 6/1986 | Hatch |
| 4,999,190 | 3/1991 | Fina et al. |

OTHER PUBLICATIONS

Amber-hi-lites-No. 177 Summer 1985-Kunin.
Fina, Louis R. & Jack L. Lambert, "A Broad-Spectrum Water Disinfectant that Releases Germicide on Demand", Proceedings Second World COngress, Intl. Water Resources Assn., vol. II, pp. 53-59, New Delhi, Dec. 1975.
Gerba, Charles, P. & Morteza Nakhforoosh, "Evaluation of Iodine (I2) as Tri-Iodine (I3) Resin for Inactivation of Enteric Bacteria and Viruses, and of Microfiltration for Removal of Giardia Cysts as Incorporated in the Recovery Engineering Antimicrobial Water Purifier for World Travelers: Efficacy of Antimicrobial Agents", Dept. of Microbio. & Immun. & Natr. & Food Sci., Univ. of Ariz., Tucson, Jun. 26, 1990.
Marchin, George L. & Louis R. Fina, "Contact and Demand-Release Disinfectants", C.R.C. Critical Reviews in Environmental Control, vol. 19, pp. 277-290 (1989).
United States Environmental Protection Agency, "Guide Standard and Protocol for Testing Microbiological Water Purifiers", Apr. 1987.
Excerpts from "Report of the Evaluation of a Water Purifier from Recovery Engineering, Inc.", Johns Hopkins Univ. School of Hygiene & Pub. Hlth., Div. of Disease Control, Oct. 10, 1991, Compiled by PUR, Div. of Recovery Eng. (promotional material).
Sullivan, Brian F, "Efficacy of PUR Antimicrobial Water Purifier in Eliminating Infectious Microorganisms from Contaminated Drinking Water", Jan. 1991 (promotional material).

Primary Examiner—Thurman K. Page
Assistant Examiner—Peter F. Kulkosky
Attorney, Agent, or Firm—Merchant, Gould, Smith, Edell, Welter & Schmidt

[57] ABSTRACT

The invention provides a method for preparing polyhalide resin disinfectants. The step of the method involves circulating an effective amount of a polyhalide salt carrier solution between an effective amount of elemental halide and a strong base anion exchange resin until substantially all of the resin is converted to the polyhalide form. The elemental halide and the resin are separately disposed but connected so that the polyhalide salt carrier solution can be recirculated until all of the elemental halide is transferred to the resin. The method of the invention can be used to form a tri-iodide or penta-iodide resin, or mixed form of the resin including $IBr_2^-/I_2^-$.

7 Claims, 1 Drawing Sheet

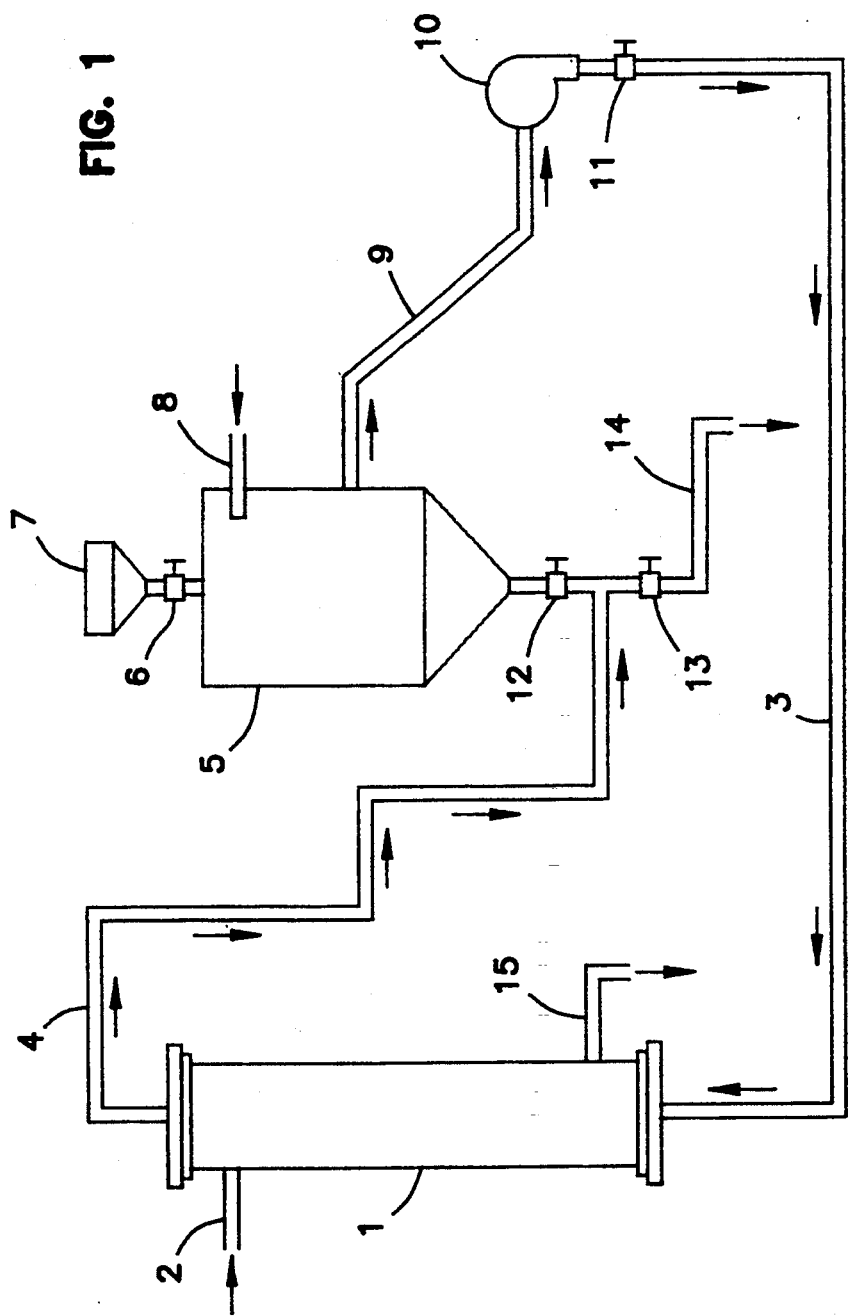

METHOD FOR PREPARING POLYHALIDE RESIN DISINFECTANTS

BACKGROUND OF THE INVENTION

Disinfectants can be defined as chemical agents that kill pathogenic organisms on inanimate objects. Disinfection is directed against viruses, bacteria and eukaryotic parasites, such as Giardia. Traditional disinfectants act in dilute solution by diverse mechanisms to kill microorganisms. When applied to drinking water, traditional disinfectants are undesirable because they generally leave rather high residual concentrations of the disinfectant in the water. Typical disinfectants include chlorine gas, aqueous iodine, aqueous silver nitrate, hydrogen peroxide, phenol, ethanol, and benzalkonium chloride.

Solid phase disinfectants are available that require that the pathogenic microorganisms contact a biocidal surface. Some of these disinfectants act without any measurable release of a chemical agent and are known as "contact disinfectants". Others contain traditional disinfecting agents in slow release formulations and are known as "constant release disinfectants". Finally, some solid phase disinfectants release a toxic dose of disinfectant to microorganisms upon contact, leaving very little residual disinfectant in the solution in the absence of any microorganisms and are called "demand release disinfectants".

Well known demand release type disinfectants include polyiodide resins. Polyiodide resins inactivate a wide variety of microorganisms including Giardia cysts leaving a very small residual amount of iodine in the treated solution. These types of resins are very stable and have been used in portable water purifiers, home water purifiers, and by the U.S. Space Program. G. L. Marchin et al., "Contact and Demand Release Disinfectants" in *C.R.C. Critical Reviews in Environmental Control*, 19:227 (1989).

Known methods for preparing polyiodide resins are not readily adapted to industrial scale production. For example, batch methods involving stirring the resin beads for 24 hours with a solution of $I_3^-$ are described in U.S. Pat. Nos. 3,817,860 and 3,923,665. The $I_3^-$ solution is formed by mixing elemental iodine with potassium iodide. These batch methods are not suitable for industrial use because of the difficulty of mixing large scale amounts of elemental iodine with potassium iodide without causing iodine recrystallization and because they require excessive amounts of reagents. Improper preparation of resin in this manner can produce a high polyiodide residual in the treated effluent and result in incrustation of elemental iodine within the resin bed.

A method for producing polyiodide resins using a fluidized bed system is described in U.S. Pat. No. 4,238,477. In this method, water free of halide ions is used as a carrier to apply elemental iodine gradually and uniformly to the resin. However, this process would require a very large expenditure on capital equipment, and would be quite expensive to operate. First of all, to obtain processing times which are less than several days running time, temperatures close to the boiling point of the water solution are required. Consequently, pressure vessels are required which could handle the large pressures which would develop should the temperature go a bit too high. In addition, corrosion resistant materials such as glass and Teflon are required to offset the caustic effects of the hot iodine solution. Such elevated temperatures will also cause a partial pressure of $I_2$ vapor, which is potentially hazardous. As a result, the cost of capital equipment involved in such a process would be prohibitively large. Furthermore, heating and maintaining a constant temperature throughout the system to avoid precipitation of iodine on any of the surfaces contacted by the solution for such long processing times would be extremely expensive in a large-scale system.

Thus, there is a need to develop a method for producing a polyhalide resin disinfectant that is less prone to safety-related problems, is more cost efficient, and is easier to manufacture on an industrial scale.

SUMMARY OF THE INVENTION

A method of the invention involves using a polyhalide salt carrier solution to transfer an effective amount of an elemental iodine or bromine to a strong base anion exchange resin to convert the resin to the polyhalide form, preferably in a closed loop system. A polyhalide resin disinfectant can include a single polyhalide anion or a mixed form containing at least two different polyhalide anions. Preferably, the polyhalide resin disinfectant is a triiodide ($I_3^-$), pentaiodide ($I_5^-$), tribromide ($Br_3^-$), $IBr_2^-$, $BrI_2^-$, and mixtures thereof. The especially preferred resins are $I_3^-$, $I_5^-$, and the $IBr_2^-$ resins.

The step of the method involves circulating an effective amount of a polyhalide salt carrier solution between an effective amount of an elemental iodine or bromine and a strong base anion exchange resin until substantially all of the resin is converted to the polyhalide form. The elemental iodine or bromine and the resin are separately disposed, preferably in separate containers. The strong base anion exchange resin is converted if necessary to the iodide $I^-$ or bromide $Br^-$ form. The method of the invention can be used to form a polyhalide resin disinfectant in an efficient manner without causing recrystallization of the elemental iodine or bromine in the resin, particularly on an industrial scale.

When a mixed form of the polyhalide resin is prepared, the circulating step comprises circulating the polyhalide salt carrier solution between an effective amount of a first elemental halogen and the resin, followed by a second elemental halogen and the resin. The polyhalide salt carrier solution circulates between the first elemental halogen and the resin until the resin is converted to a first polyhalide form and an unconverted form. The unconverted form of the resin is then converted by circulating a polyhalide carrier solution between a second elemental halogen and the resin until substantially all of the resin is converted to a polyhalide form. The preferred elemental halides are iodine and bromine. The preferred mixed form polyhalide resin disinfectants include mixtures of $BrI_2^-$, $IBr_2^-$, $IBr_2^-/I_3^-$, $BrBr_2^-/I_3^-$, and $I_3^-/I_5^-$ mixtures.

The strong base anion exchange resin contains strongly basic groups such as quaternary ammonium groups, amine groups, sulfonium groups, or phosphonium groups. The resin is preferably a quaternary ammonium anion exchange resin. Commercially available resins are typically in the chloride or sulfate form and are converted to the $I^-$ or $Br^-$ form by contact with a soluble halide salt. The halide salt is formed and circulated through the resin until substantially (95% or greater) all of the resin is converted to the $I^-$ or $Br^-$ form. Suitable halide salts include calcium iodide, calcium bromide, magnesium iodide, magnesium bromide, sodium iodide, sodium bromide, and preferably potassium iodide or bromide.

Once converted to the $I^-$ or $Br^-$ form, the polyhalide form of the resin is produced by circulating a polyhalide carrier solution through the resin. The polyhalide carrier solution is formed by contacting an effective amount of elemental iodine or bromine with an effective amount of a polyhalide salt carrier solution. An effective amount of the elemental iodine or bromine is that amount that provides for conversion of substantially all of the resin to the polyhalide form. An effective amount of the polyhalide salt carrier solution is that amount that provides for dissolution of a portion of the elemental iodine or bromine, and preferably dissolution of at least about 1000 ppm of the elemental halide for given flow conditions. Suitable polyhalide salt carrier solutions include solutions of sodium iodide, sodium bromide, potassium bromide, magnesium bromide, magnesium iodide, calcium bromide, calcium iodide, and potassium iodide. The preferred polyhalide salt carrier solution is about a 0.01M to about 2M potassium iodide or bromide solution. The polyhalide carrier solution functions to transfer the elemental iodine or bromine to the resin and is circulated between the elemental iodine or bromine and the resin until substantially all of the resin is converted to the polyhalide form or substantially all of the elemental iodine or bromine is transferred to the resin.

Once formed, the polyhalide resin is tested for its specific gravity, residual halide in the effluent from a test cartridge containing the resin, and the capacity to inactivate microorganisms. The polyhalide resin disinfectants can then be used for water purification.

BRIEF DESCRIPTION OF THE FIGURES

FIG. 1 is a schematic diagram depicting a closed loop apparatus and overall process embodying a method for preparing a polyhalide resin disinfectant according to the present invention.

DETAILED DESCRIPTION OF THE INVENTION

The invention provides a method for preparing a polyhalide resin disinfectant that is easy, efficient, and does not result in the recrystallization of elemental iodine, especially on an industrial scale. A method of the invention involves the step of circulating an effective amount of a polyhalide salt carrier solution between an effective amount of elemental iodine or bromine and a strong base anion exchange resin until substantially all of the resin is converted to the polyhalide form or substantially all of the elemental iodine or bromine is transferred to the resin. Preferably, the polyhalide resin is formed using a closed loop system, such as that shown in FIG. 1.

Strong base ion exchange resins include resins that contain strongly basic groups such as quaternary ammonium, sulfonium or phosphonium groups. Specific examples of strong base resins are tertiary sulfonium resins, quaternary phosphonium resins, alkyl pyridinium resins, and quaternary ammonium anion exchange resins. The preferred resin is a quaternary ammonium anion exchange resin.

Before converting the resin to a polyhalide form the resin's capacity is determined by standard methods if not supplied by the manufacturer. The equivalent exchange capacity of the resin is a measure of the anion binding sites per milliliter of resin and is reported as milliequivalents per ml of resin. A milliequivalent is equivalent to 1/1000 of a mole. It is then preferably loaded into the resin storage container (1), such as shown in FIG. 1, through the resin intake conduit (2) in a closed loop apparatus.

Optionally, the strong base anion exchange resin is converted to the iodide $I^-$ or bromide $Br^-$ form, if necessary. Typically, the resins are commercially available in either the chloride or sulfate form. The chloride and sulfate ions are displaced with $I^-$ or $Br^-$ by contacting the resin with a soluble halide salt. A solution containing an amount of halide salt sufficient to convert substantially (90% or greater) all of the resin to the $I^-$ or $Br^-$ form is prepared and circulated through the resin. The amount of halide salt sufficient to convert the salt to the $I^-$ or $Br^-$ form can be determined by multiplying the calculated equivalent exchange capacity of the resin by the volume of resin to be converted. The amount of halide salt in solution is an amount that is at least about a 1:1 ratio with the equivalent exchange capacity of the resin to be converted to the $I^-$ or $Br^-$ form. Specific examples of suitable halide salts include sodium, magnesium, calcium, lithium, and potassium iodide or bromide. The preferred salt is potassium iodide or bromide.

When the resin is present in a closed loop apparatus, as shown in FIG. 1, preferably the halide salt solution is formed in the solution storage container (5) by adding an effective amount of the solid halide salt through the solution storage container intake reservoir (7) to deionized water present in the solution storage container (5). The halide salt solution is circulated through the resin in the resin storage container (1), preferably by means of the pump (10), until substantially all of the resin is converted to the $I^-$ or $Br^-$ form. Typically, it takes about 2 hours to convert a quaternary ammonium anion exchange resin to the $I^-$ or $Br^-$ form using the preferred closed loop apparatus.

Once converted to the $I^-$ or $Br^-$ form, the resin can then be converted to the polyhalide form by contact with a polyhalide salt carrier solution. Optionally, the resin can be washed with deionized water before contact with the polyhalide salt carrier solution. A polyhalide salt carrier solution is formed by contacting an effective amount of an elemental iodine or bromine with an effective amount of a halide salt solution. The polyhalide salt carrier solution functions to transfer elemental iodine or bromine to the resin to produce the polyhalide form of the resin.

A polyhalide resin disinfectant can be formed having a single type of polyhalide anion or as a mixed form containing at least two different types of polyhalide anions. A single type of polyhalide anion can be a trihalide or pentahalide form, e.g. $I_3^-$ or $I_5^-$. A single type of polyhalide anion can contain a single halide or mixtures of at least two different halides, e.g. $I_3^-$ or $IBr_2^-$. The preferred trihalide anions include $I_3^-$, $Br_3^-$, $IBr_2^-$, and $I_2Br^-$. A mixed form of the resin contains proportions of at least two different types of polyhalide anions, e.g. mixtures of $I_3^-$ or $I_5^-$, or $IBr_2^-$ or $I_3^-$. The two different polyhalide anions can contain the same halide as in the case of mixtures of $I_3^-$ or $I_5^-$, or can contain at least two different halogens as in the case of mixtures $IBr_2^-$ and $I_3^-$. Preferably, the mixed form of the resin contains a first polyhalide form and a second polyhalide form. The first and second elemental halide can be the same halogen or different halogens. An effective amount of the elemental halide depends on the desired form of the resin, and is that amount that is sufficient to convert substantially all (95% or greater) to the desired polyhalide form.

When the resin is to be converted to a form having a single type of polyhalide anion, an effective amount can be calculated by determining the equivalent exchange capacity of the resin. For example, when the resin is to be converted to a trihalide form, an effective amount of elemental iodine or bromine is an amount that is about a 1:1 ratio with the equivalent exchange capacity of the resin to be converted. If the resin is to be converted to a pentahalide form, then an effective amount of elemental iodine or bromine is an amount that is about a 2:1 ratio with the equivalent exchange capacity of the resin to be converted.

If a mixed form of the resin is desired, an effective amount of elemental iodine or bromine depends on the equivalent exchange capacity of the resin to be converted and the proportion of each type of polyhalide anion desired in the final resin product. The equivalent exchange capacity of the resin to be converted is calculated and then multiplied by the desired proportion of each type of polyhalide anion. The proportion of each polyhalide anion form results in a mixed form of the resin that can kill at least 7 logs of *Klebsiella terragina*, release less than 20 ppm residual halogen in the effluent, and is stable under filter operating conditions. Typical filter operating conditions are described in Example 3 and include passing 100 gallons or 370 liters of water per cubic inch of resin through a filter under ambient temperatures (20°-25° C.) at 1 liter/minute.

Mixed forms of the resin that contain polyhalide anion complexes of chlorine or fluorine are typically not suitable because these polyhalide anions are readily eluted from the column under filter operating conditions resulting in a high level (greater than 20 ppm) of residual halogen in the effluent. While not in any way meant to limit the invention, it is believed that a suitable mixed form of the resin balances efficacy of killing microorganisms with the amount of residual halogen released in the effluent. For example, it is known that $I_5^-$ is more effective in killing of Giardia cysts but also results in a high level of residual iodine in the effluent. A mixed form of the polyhalide resin disinfectant contains an amount of $I_5^-$ sufficient to increase the effectiveness of killing of Giardia without increasing the levels of residual or iodine greater than 20 ppm and, more preferably, no greater than about 5-10 ppm, and most preferably, no greater than 1 ppm. A mixed form of the resin having a polyhalide anion containing iodine and a polyhalide anion containing bromine also preferably balances efficacy of killing microorganisms with the residual halogen released into the effluent. Preferably, this mixed form of the column contains about 50-95% of a polyhalide anion containing iodine and about 5-50% of a polyhalide anion containing bromine.

Once the desired proportion of each polyhalide anion form of the mixed form of the resin is identified, an effective amount of elemental iodine or bromine can be determined by multiplying the molar equivalent exchange capacity of the resin by the desired proportion of the polyhalide anion. If the polyhalide anion form is a trihalide then the effective amount of elemental halide is that amount that is a 1:1 ratio with the proportion of the molar equivalent exchange capacity of the resin. If the polyhalide anion form is a pentahalide, the effective amount of the elemental halide is that amount that is about a 2:1 ratio with the proportion of the molar equivalent exchange capacity of the resin. For example, if the desired mixed form of the resin has 50% of the first polyhalide form containing $I_3^-$ polyhalide anion and 50% of a second polyhalide form containing an $I_5^-$ polyhalide anion, the effective amount of elemental iodine to form the first polyhalide form is calculated by multiplying the molar equivalent exchange capacity by 0.5, and the effective amount of elemental iodine would be equal to that molar amount (1:1 ratio). The effective amount of elemental iodine to form the second polyhalide form is calculated by multiplying the molar equivalent exchange capacity of the resin by 0.5 and then multiplying that number by two to get the pentaiodide form of the resin (2:1 ratio).

An effective amount of the halide salt solution is that amount of halide salt that provides for dissolution of a portion of the elemental iodine or bromine so that it can be transferred to the resin. Preferably, the halide salt solution contains the same halide as the elemental iodine or bromine so that the elemental halide readily dissolves to form polyhalide anions. If the halide salt solution contains a different halide from the elemental iodine or bromine, it is more difficult to form a polyhalide anion because of redox reactions.

An effective amount of the halide salt solution can be determined by contacting various concentrations of the halide salt solution with an elemental iodine or bromine and then determining the level of free halide by standard Hach test, as described in the *Hach Water Analysis Handbook*. Concentrations of halide salt solutions that dissolve at least about 1000 ppm elemental iodine or bromine are preferable and about 1000-200,000 ppm elemental halide are more preferable. Specific examples of halide salts include sodium iodide, sodium bromide, potassium bromide, potassium iodide, magnesium iodide, magnesium bromide, calcium iodide, and calcium bromide. The preferred halide salt solution is about a 0.01M to 2M potassium iodide or bromide solution. Potassium iodide is preferred to form a polyiodide anion and potassium bromide is preferred to form a polybromide anion.

The polyhalide salt carrier solution functions to transfer the elemental iodine or bromine to the resin by circulating the polyhalide carrier solution from the elemental iodine or bromine to the resin. The preferred elemental halide is selected from the group of iodine, bromine, and mixtures thereof. The elemental iodine or bromine and the resin are separately disposed, preferably in separate containers. Although preferred, the resin and elemental iodine or bromine do not have to be in separate containers. For example, they may be present in different positions of a single closed loop conduit. After moving through the resin, the polyhalide carrier solution is returned to the remaining solid elemental iodine or bromine and then circulated back to the resin. This circulation of the polyhalide carrier solution continues until substantially all of the resin is converted to the polyhalide form and/or substantially all of the elemental iodine or bromine is transferred to the resin. Preferably, the recirculation continues for at least about 4-8 hours or until the polyhalide carrier solution going to the resin is substantially the same light yellow color as the solution going back to the elemental iodine or bromine.

When a mixed form of the resin is prepared, the circulating step is conducted so as to achieve a polyhalide resin having a proportion of at least two different types of polyhalide anions. A proportion of the resin is formed in a first polyhalide form by circulating an effective amount of a polyhalide carrier solution between an effective amount of a first elemental halogen and the resin. The remaining portion of the resin is in an unconverted form. An unconverted form of the resin is a resin that typically is in the I− or Br− form, but has not yet formed a polyhalide complex with an anion such as a trihalide or pentahalide anion. The unconverted form of the resin is then converted to a second polyhalide form. The second polyhalide form is different than the first polyhalide form with respect to either the halide composition or the form of anion, i.e. trihalide anion or pentahalide anion. The second polyhalide form is formed by circulating an effective amount of the polyhalide salt carrier solution between a second elemental halogen and the resin until substantially all of the resin is in a polyhalide form. The first and second elemental halogen can be the same if the two different polyhalide anions differ in the form of the anion, i.e. trihalide or pentahalide. The first and second elemental halogen can be different if the two different polyhalide anions differ in halide composition, e.g. $IBr_2^-$ and $I_3^-$. In a preferred version, the mixed form of the column comprises 50% $I_3^-$ and 50% $I_5^-$.

In the preferred version, a polyiodide resin disinfectant is formed. An effective amount of elemental iodine is placed into the solution storage container (5) through the solution storage container intake reservoir (7) and valve (6). Deionized water is added to fill the solution storage container (5) from the deionized water intake conduit (8). A halide salt solution is then formed in the solution storage container (5) by adding an effective amount of halide salt to the deionized water in the solution storage container (5). The halide salt solution contacts and dissolves a portion of the elemental iodine in the solution storage container to form a polyhalide salt carrier solution.

The elemental iodine and the resin are separately disposed, preferably as shown in FIG. 1. The elemental iodine is located in the solution storage container (5) and the resin is in the resin storage container (1). The polyhalide salt carrier solution in recirculated from the solution storage container (5) by means of the pump (10) and the carrier solution feed conduit (3). After the polyhalide carrier solution contacts the resin, it circulates back to the elemental iodine through the carrier solution return conduit (4) and valve (12) back to the solution storage container (5). The polyhalide carrier solution contacts the remaining solid elemental iodine and then is recirculated back to the resin until substantially all of the elemental iodine is dissolved and transferred to the resin. The polyhalide form of the resin is removed from the resin storage column (1) by means of the product discharge conduit (15).

Once the polyhalide resin is prepared, it is optionally washed with water. The polyhalide resin is tested for its specific gravity, residual $I_2$ in the effluent of a test cartridge, and efficacy for killing of microorganisms. Specific gravity of the resin is determined by standard methods and indicates the type and homogeneity of the resin. A triiodide resin having about 95% tri-iodide groups has a specific gravity of about 1.5 to 1.6. A penta-iodide resin having about 95% penta-iodide groups has a specific gravity of about 1.7 to 1.8. The efficacy of the polyhalide resin against other bacteria, viruses, and eukaryotic protozoans can be assessed by standard methods.

A penta-iodide resin can be formed according to the preferred method disclosed herein. When the penta-iodide resin is to be formed, the effective amount of elemental iodine is increased from about a 1:1 ratio with the equivalent exchange capacity of the resin to about a 2:1 ratio. In addition, the polyhalide carrier solution is typically circulated until substantially all of the elemental $I_2$ is transferred to the resin, preferably about 8–12 hours. When the penta-iodide resin is formed, the circulation time for the polyhalide carrier solution is typically double the amount of time it takes to form the tri-iodide resin.

EXAMPLE 1

Preparation of Tri-Iodide ($I_3^-$) and Penta-Iodine Resin ($I_5^-$)

A tri-iodide resin was formed by contacting a strong base quaternary ion exchange resin with a polyhalide carrier solution of tri-iodide ion ($I_3^-$) in a closed loop apparatus as shown in FIG. 1.

Quaternary ion exchange beads of known equivalent exchange capacity were loaded into a resin storage container (1) and converted to the I− form by contacting a potassium iodide solution. A solution storage container (5) was filled with about 51 gallons of 0.76M KI solution. An additional 20 lb of the potassium iodide was dissolved in about 4–5 gal deionized water and stored for about 2–10 hours.

The KI solution was pumped from the solution storage container (5) by means of the pump (10) and conduit (3) into the resin storage container (1) and then was returned to the solution tank by way of a solution return conduit (4). The potassium iodide solution was continuously recirculated through the resin in the storage container (1) for about 2 hours. Then, the solution tank was drained through the waste water discharge valve (13) and conduit (14). The solution tank (5) was refilled with deionized water and the resin washed with deionized water for about 30 to 60 minutes. The solution was then drained. The solution tank (5) was refilled with deionized water from the deionized water conduit (8).

The solution of potassium iodide in deionized water (20 lb in about 5 gal of deionized water) prepared earlier was added to the solution tank (5) to form about a 0.28M iodide carrier solution for the iodine ($I_2$). About 72 lbs of elemental iodine ($I_2$) was then placed into the solution tank (5) through the solution tank reservoir (7) and intake valve (6). The pump (10) was then turned on. The iodide carrier solution contacted the iodine ($I_2$) to form $I_3^-$ ions, which were then pumped into the resin storage container (1). The carrier solution was recirculated through the column (1) and back to the solution storage container (5) for about 4–5 hours, until the solution going into the column matched the light yellow color going out of the column. The resin was then rinsed with water for about 10 min and the polyiodide resin was drained through the product discharge conduit (15).

A penta-iodide resin was formed using the same process steps, except that the amount of an elemental iodine ($I_2$) added to the solution storage container was double that for the $I_3^-$ resin (about 144 lbs).

EXAMPLE 2

Solubility of Iodine as a Function of Potassium Iodide Concentration Compared with Solubility of Iodine as a Function of Temperature To determine the solubility of elemental iodine ($I_2$) as a function of the concentration of potassium iodide salt solution, iodine was mixed with solutions of increasing concentrations of potassium iodide. The amount of iodine dissolved in the potassium iodide solution was determined by the standard Hach test, as described in *Hach Water Analysis Handbook*.

Two liters of purified deionized water were stirred in a flask with a magnetic stir bar. Solid iodine was added to the water so that there was at least 30 gm of solid iodine in the bottom of the flask. After 30 min, a 1 ml sample was taken and serially diluted 10-fold and the level of free iodine in parts per million (ppm) determined by the Hach test. Potassium iodide was added incrementally, and a sample was taken again after 30 min. The sample was serially diluted 10-fold and the amount of free iodine in ppm was detected using the Hach method. All solutions were at room temperature (approximately 70° F.).

The results are shown in Table I.

TABLE I

Solubility of $I_2$ as a Function of KI Concentration

| | KI (M) | $I_2$ (ppm) |
|---|---|---|
| 1 | 0.000 | 82.300 |
| 2 | 0.003 | 215.000 |
| 3 | 0.005 | 369.000 |
| 4 | 0.007 | 1002.000 |
| 5 | 0.013 | 1146.000 |
| 6 | 0.025 | 1360.000 |
| 7 | 0.050 | 1539.000 |
| 8 | 0.125 | 18616.000 |
| 9 | 0.250 | 35800.000 |
| 10 | 0.500 | 71600.000 |
| 11 | 0.750 | 118140.000 |
| 12 | 1.000 | 142000.000 |

The results indicate that as the concentration of potassium iodide increased, the amount of elemental iodine $I_2$ dissolved increased. The amount of $I_2$ dissolved increased to greater than 1000-fold than that of the solubility of iodine in water without any halide ions.

The solubility of potassium iodide in deionized water (free of any halide ions) as a function of temperature was also measured. Two liters of deionized water were stirred and 60 gm of solid iodine was added to the water. The solution was heated using a closed loop temperature controller at a rate to cause a temperature rise of about 8-10° F. per hour. Every 30 min a 1 ml sample was taken and the temperature recorded at the sampling time. The sample was serially diluted 10-fold and the amount of dissolved iodine in ppm was determined by the Hach test. The results are shown in Table II.

TABLE II

Solubility of $I_2$ as a Function of Temperature

| Temperature (°F.) | $I_2$ (ppm) |
|---|---|
| 70 | 82 |
| 82 | 179 |
| 84 | 258 |
| 87 | 347 |
| 96 | 422 |
| 108 | 519 |
| 124 | 591 |

TABLE II-continued

Solubility of $I_2$ as a Function of Temperature

| Temperature (°F.) | $I_2$ (ppm) |
|---|---|
| 140 | 823 |
| 150 | 967 |
| 164 | 1074 |
| 174 | 1611 |
| 190 | 2255 |
| 200 | 2613 |

The results indicated that under room temperature conditions, only a very small amount of iodine dissolved (82 ppm). By increasing the temperature, the amount of iodine dissolved was increased up to about 400-fold to about 2600 ppm.

A comparison of the solubility of iodine as a function of potassium iodide concentration vs. temperature shows that dissolution of elemental iodine in potassium iodide was much greater than that of water alone (i.e., free of halide ions) at any temperature. The transfer rate of $I_2$ in a potassium iodide salt solution provides for formation of the tri-iodide resin in about 8 hours processing time. In contrast, the transfer rate of $I_2$ in water with heat, up to 160° F., would take about 47 hours (or 2 days) of continuous processing time. Thus, using potassium iodide solution as a carrier for the $I_2$ was much more efficient at solubilizing the $I_2$ than water free of halide ions using heat.

Furthermore, the use of heat to solubilize $I_2$ leads to excessive vapor pressure of the elemental iodine at elevated temperatures. An indication of this is given by the thermodynamic relationship between the vapor pressure of pure $I_2$ as a function of temperature is given by $$\ln P = \frac{-8240}{T} - 2.51 \ln T + 34.164 \quad (P = \text{atm}, T = °K.)$$

as described in *Metallurgical Thermodynamics*, editor Gaskell (1981). A calculation of the vapor pressures of $I_2$ at the temperatures shown in Table II is shown in Table III.

TABLE III

| Temperature (°F.) | Vapor Pressure of $I_2$ (Torr) |
|---|---|
| 70.0 | 0.23 |
| 82.6 | 0.41 |
| 84.5 | 0.45 |
| 87.0 | 0.50 |
| 96.0 | 0.74 |
| 108.0 | 1.24 |
| 124.0 | 2.37 |
| 140.0 | 4.37 |
| 150.0 | 6.29 |
| 164.0 | 10.26 |
| 174.0 | 14.35 |
| 190.0 | 24.00 |
| 200.0 | 32.66 |

The results in Table III show that the application of heat to elemental iodine causes its vapor pressure to rise appreciably. This upward trend applies equally well to solutions of iodine. Such vapor pressures could lead to hazardous conditions should a leak occur in the system and could present a significant risk of exceeding OSHA air quality standards.

In sum, because the solubility of iodine in hot water free of halide ions is so much below that of room temperature solutions which contain halide ions, the processing times required in making a given amount of resin are much greater. The cost of maintaining this system at temperature for this long period of time would be excessive and would require round-the-clock supervision. In addition, the elevated temperatures necessary for such a system would require heavy duty pressure vessels to contain iodine vapors, since there would be a chance that the boiling point of water would be exceeded. Any equipment surfaces contacted by such a hot and caustic solution would have to consist of corrosion resistant materials such as glass or Teflon. Consequently, a large scale system based on an elevated temperature process is inferior to one based on this new room temperature process.

EXAMPLE 3

Properties of $I_3^-$ or $I_5^-$ Resin Formed in Accordance with the Method of the Invention The properties of the $I_3^-$ or $I_5^-$ polyhalide resins are examined by determining the specific gravity of the iodinated resin, the ability of the resin to kill microorganisms, and the residual $I_2$ remaining in the effluent passing from a test column.

Specific Gravity

The specific gravity of a sample of the $I_3^-$ or $I_5^-$ resin prepared as in Example 1 was determined as follows. About 90 ml of the iodinated resin beads were immersed in water in 100 ml graduated cylinder and weighed. Weights of the water above the beads in the graduated cylinder were subtracted. The $I_3^-$ resin having at least 95% $I_3^-$ groups has an expected specific gravity of about 1.5 to 1.6. The $I_5^-$ resin having at least about 95% $I_5^-$ groups has an expected specific gravity of about 1.7 to 1.8. The results from testing batches $I_3^-$ or $I_5^-$ resin are shown in Table IV.

TABLE IV

| | $I_3^-$ or $I_5^-$ Resin Testing | |
|---|---|---|
| | Batch No. | Specific Gravity |
| $I_3^-$ Resin | 071692-1 | 1.59 |
| | 111692-1 | 1.56 |
| | 120192-1 | 1.58 |
| $I_5^-$ Resin | 060992-1 | 1.76 |
| | 111792-3 | 1.77 |
| | 112092-1 | 1.77 |

Microbiological Testing

To qualify as a microbiological water purifier under E.P.A. standards, a water purifier unit "must remove, kill or inactivate all types of disease causing microorganisms from the water including bacteria, viruses and protozoan cysts so as to render the processed water safe for drinking." Preferably, the purified water also has a very low level of residual disinfectant present. Water purifiers containing $I_3^-$ resin with a specific gravity of about 1.5 to about 1.6 have been tested extensively using E.P.A. protocols and have passed.

Water purifiers containing a tri-iodide resin, a microfilter and a pump were tested by the University of Arizona using the E.P.A. Guide Standard. The tri-iodide resin has the same specific activity as shown in Table IV, but was prepared by a different method. The E.P.A. requirements for microbiological killing are shown in Table V.

TABLE V

E.P.A. Microbiological Reduction Requirements For Representative Organisms

| Organism | Influent Challenge | Minimum Required Reduction | |
|---|---|---|---|
| | | Log | Percentage |
| Bacteria: | | | |
| Klebsiella terrigena | $10^7$/100 ml | 6 | 99.9999 |
| Virus: | | | |
| a. Poliovirus 1 (LSc) | $10^7$/L | 4 | 99.99 |
| b. Rotavirus (SA-11) | $10^7$/L | 4 | 99.99 |
| Cyst (Protozoan): | | | |
| Giardia muris or Giardia lamblia | $10^6$/L | 3 | 99.9 |

The methods for testing and quantitating the presence of these microorganisms in test samples are described in the United States Environmental Protection Agency "Guide Standard and Protocol for Testing Microbiological Water Purifiers", April 1987, available from the U.S. Environmental Protection Agency Library in Seattle, Wash.

The University of Arizona tested water samples at various times and with various loads of solids and organic materials in water purifiers containing the tri-iodide resin, in accordance with E.P.A. Guide Standard. Briefly, three water purifier units obtained from Recovery Engineering Company containing tri-iodide resin were operated according to the manufacturers' instructions until the design lifetime of 100 gallons or 370 liters of water was passed through the units. The units were challenged with Poliovirus Type 1, Rotavirus I, Hepatitis A, Klebsiella terriqena, and Giardia lamblia after passage of 0, 5, 75, and 100 gallons of water through the units. The units were also tested for "worst case" water quality after passage of 75 and 100 gallons of water. The "worst case" water passed through after 75 gallons contained 1500 mg/l dissolved solids, 10 mg/l organic matter, a turbidity of 30 NTU, and pH=9.0. For the 100-gallon lifetime test, the "worst case" water quality was the same as that at 75 gallons, except the pH=5.0. After the challenge organism was passed, the effluent was measured for percentage of organisms removed. The results are shown in Table VI.

TABLE VI

Summary Test Results for University of Arizona Tests

| Organism | Average Influent Challenge | Average Percent Removal[1] |
|---|---|---|
| Klebsiella terrigena | $1.8 \times 10^9$/L | >99.9999 |
| Poliovirus 1 (LSc) | $3.6 \times 10^7$/L | >99.99 |
| Rotavirus (SA-11) | $1.0 \times 10^7$/L | >99.99 |
| Hepatitis A | $1.0 \times 10^7$/L | >99.99 |
| Giardia lamblia[2] | $1.2 \times 10^6$/L | >99.99 |

[1]These were averaged over the seven data points taken.
[2]Efficacy in killing Giardia lamblia was achieved in these purifiers by a design which incorporates a 3 to 4 micron microfilter upstream of the I3 resin bed.

The results show that the water purifiers meet or exceed the standards set in the EPA protocol. Although the tri-iodide resin used in these tests was prepared by a different method than that described in Example 1, it is believed that the $I_3^-$ resin prepared as in Example 1 has the same characteristics as the more extensively characterized $I_3^-$ resins because the polyhalide resins prepared by the method of the invention have substantially the same composition and specific gravity. Furthermore, bridging tests, such as the one that follows, confirm the resin's efficacy in killing microorganisms.

To confirm the efficacy of the polyhalide resin formed in accordance with Example 1, the $I_3^-$ resin was tested for the ability to kill *Klebsiella terrigena*, a representative bacteria known for its virulence. The volume of polyhalide resin and flow rate during such tests accurately represent the conditions under which the water purifier units previously tested by University of Arizona were operated.

Briefly, two columns of $I_3^-$ resin from the production batch were tested. One sample of the resin was taken from the top of the column and one sample taken from the bottom of the column. Standard test influent contained $10^8$ *Klebsiella terrigena* organisms/ml and was pumped through the column at 1 liter/min. Sodium thiosulfate (100 ppm) was added to neutralize free iodine in the effluent after collecting each sample. The 400 ml effluent samples were then plated and counted. The results are shown in Table VII.

TABLE VII

Standard Resin Batch Efficacy (Batch 062992)
(Influent Conc. $1.7 \times 10^8$/L)

| Sample Identify | 0.2 ml of 1/20 | 0.2 ml | 10 ml | 100 ml | calc. density of *Klebsiella terrigena* |
| --- | --- | --- | --- | --- | --- |
| 062992 TOP, DI | 0 | 0 | 0 | 0 | $<1.0 \times 10^1$/L |
| 062992 BOT, DI | 0 | 0 | 0 | 0 | $<1.0 \times 10^1$/L |

The results show that the tri-iodide resin prepared as described in Example 1 was able to eliminate greater than 7 log (greater than 99.99999%) of bacteria present in the standard test sample. Thus, it is believed that the $I_3^-$ resin prepared as in Example 1 has the same characteristics as the tri-iodide resin tested by the University of Arizona and effectively kills microorganisms.

Residual $I_2$ Measurement

The $I_3^-$ and $I_5^-$ resins prepared as described in Example 1 were also tested for the amount of residual iodine in the effluent obtained from a test cartridge under conditions representing those of actual use. The amount of free iodine was measured using the standard Hach test kit (as described in the *Hach Handbook of Water Analysis*) and multiplying the results by 3.58, the ratio of molecular weights of $I_2/Cl_2$. The effluent from the $I_3^-$ resin measured at 1 ppm free iodine and the effluent from the $I_5^-$ resin typically has a 9 ppm residual level of free iodine. Water purifiers containing the $I_5^-$ resin typically contain a carbon filter that acts to scavenge residual $I_2$ from the effluent.

EXAMPLE 4

Preparation and Testing of $IBr_2$ Resin

The $IBr_2^-$ resin was formed by contacting a strong base quaternary ion exchange resin with a polyhalide carrier solution of tri-bromide ion ($Br_3^-$) in a closed loop apparatus, as shown in FIG. 1.

Quaternary ion exchange beads of known equivalent exchange capacity were loaded into a resin storage container (1) and converted to the $I^-$ form by contacting the potassium iodide solution. The potassium iodide solution in the solution storage container (5) was a 0.14M KI solution.

The KI solution was pumped from the solution storage tank and was continuously recirculated through the resin in the storage container (1) for about 1 hour. Then, about 60 grams of KBr was added to the solution tank (5) to form about a polyhalide carrier solution of 0.20M KBr solution for the elemental bromine ($Br_2$).

About 59.5 grams of elemental bromine ($Br_2$) was then placed into the solution tank (5) through the solution tank reservoir (7) and intake value (6). The pump (10) was then turned on. The bromide carrier solution contacted the bromine ($Br_2$) to form $Br_3^-$ ions, which were then pumped into the resin storage container (1). The carrier solution was recirculated through the column (1) and back to the solution storage container (5) for about 1.75 hours, until the solution going into the column matched the light yellow color going out of the column. The resin was then rinsed with water for about 10 minutes and the $IBr_2^-$ resin was drained through the product discharge conduit (15).

This batch of resin was subsequently tested for efficacy against *Klebsiella terrigena*, a representative bacteria known for its virulence. The volume of polyhalide resin and flow rates used accurately represent those which would be used for such a resin in a commercial product. Standard test influent contained $1.25 \times 10^{11}$ *Klebsiella terrigena* organisms/ml and was pumped through the column directly into concentrated sodium thiosulfate. The 400 ml effluent samples were then plated and counted. The results are shown in Table VIII.

TABLE VIII $IBr_2$ Resin Batch Efficacy (Batch 012693-1)
(Influent Conc. $1.25 \times 10^{11}$/cfu/l)

| Sample Identify | 0.2 ml | 10 ml | 50 ml | calc. density of *Klebsiella terrigena* |
| --- | --- | --- | --- | --- |
| 012693-1, 1 liter/min | 0 | 0 | 0 | $<2 \times 10^1$/L (>9.8 log) |
| 012693-1, 2 liter/min | 0 | 0 | 0 | $<2 \times 10^1$/L (>9.8 log) |

The results show that a filter containing the $IBr_2^-$ was able to effectively kill greater than 7 logs of *Klebsiella terrigena*. Examples of other forms of resin that can be made via this general method include: $Br_3^-$, $BrI_2$, mixed forms $IBr_2^-/I_2^-$, $BrBr_2/I_2$.

Residual bromine $Br_2$ in the effluent was also determined as described for iodine. The 400 ml samples of effluent collected from a filter containing the $IBr_2$ resin were tested for residual bromine as described previously. A level of 0.7 ppm bromine was detected in the effluent.

While the present invention has been described in connection with the preferred embodiment thereof, it will be understood many modifications will be readily apparent to those skilled in the art, and this application is intended to cover any adaptations or variations thereof. It is manifestly intended this invention be limited only by the claims and equivalents thereof.

All patents and publication described herein are hereby incorporated by reference.

What is claimed:

1. A method of preparing a polyhalide resin disinfectant, comprising:
    (a) providing a strong base anion exchange resin in a resin storage container wherein the resin is the $Br^-$ or $I^-$ form;
    (b) adding an effective amount of elemental $I_2$ or $Br_2$ or mixture thereof to a solution storage container, the solution storage container being separate from and connected to the resin storage container;

(c) Contacting the elemental $I_2$ or $Br_2$ in the solution storage container with about a 0.01M to 2M halide salt solution to form a polyhalide salt carrier solution, wherein the halide salt solution is formed from salts bromine, salts of iodine or mixtures thereof, and wherein the polyhalide carrier solution is at ambient temperature;

(d) circulating and recirculating the polyhalide salt carrier solution between the elemental $I_2$ or $Br_2$ in the solution storage container through the resin in the resin storage container so that the elemental $I_2$ or $Br_2$ is gradually dissolved and is transferred to the resin until substantially all of the resin is converted to the polyhalide form, wherein no heat is applied throughout the circulating and recirculating step.

2. The method according to claim 1, wherein the strong base anion exchange resin is a quaternary ammonium resin.

3. The method according to claim 1, wherein the halide salt solution is selected from the group consisting of sodium iodide, sodium bromide, potassium iodide, potassium bromide, magnesium bromide, magnesium iodide, calcium bromide, and calcium iodide.

4. The method according to claim 1, wherein the polyhalide salt carrier solution is circulated for about 4 to 8 hours.

5. The method according to claim 1, wherein the effective amount of elemental $I_2$ is that amount to convert the resin to the $I_3-$ form.

6. The method according to claim 1, wherein the halide salt solution is about a 0.01M to a 1M salt solution.

7. A method of forming a mixed form of a polyhalide resin disinfectant comprising;

(a) providing a strong base anion exchange resin in a resin storage container, wherein the resin is in the $I-$ or $Br-$ form;

(b) adding an effective amount of a first elemental halogen to a solution storage container, the solution storage container being separate from and connected to the resin storage container, and wherein the first elemental halogen is $I_2$ or $Br_2$;

(c) contacting the first elemental halogen with an about 0.01M to 2M halide salt solution to form a polyhalide salt carrier solution, wherein the halide salt solution is a salt of bromine, a salt to iodine and or mixtures thereof and wherein the polyhalide salt carrier solution is at ambient temperature;

(d) circulating and recirculating the polyhalide carrier solution between the first elemental halogen and the resin so that first elemental halogen is gradually dissolved and transferred to the resin to form a first polyhalide form of the resin and an unconverted form of the resin;

(e) adding an effective amount of a second elemental halogen to the solution storage container, wherein the second halogen is different from the first halogen and is $I_2$ or $Br_2$, and contacting the second halogen with a halide salt solution to form a polyhalide salt carrier solution wherein the polyhalide salt carrier solution is at ambient temperature; and (f) circulating and recirculating the polyhalide carrier solution between the second elemental halogen and the resin so that the second elemental halogen is gradually dissolved and transferred to resin to form a mixed form of the resin having a first and second polyhalide form, wherein no heat is applied throughout the circulating and recirculating step.

* * * * *

UNITED STATES PATENT AND TRADEMARK OFFICE
CERTIFICATE OF CORRECTION

PATENT NO. : 5,431,908
DATED : July 11, 1995
INVENTOR(S) : James L. Lund

It is certified that error appears in the above-indentified patent and that said Letters Patent is hereby corrected as shown below:

Column 2, line 55, delete "halides" and insert therefor --halogen--.

Column 3, line 17, delete "halide" and insert therefor --iodine or bromine--.

Column 4, line 68, delete "halide" and insert therefor --iodine or bromine--.

Column 12, line 33, delete "terriqena" and insert therefor --terrigena--.

Column 14, line 30, delete "Cone" and insert therefor --Conc.--.

Signed and Sealed this

Fifth Day of March, 1996

Attest:

BRUCE LEHMAN

*Attesting Officer*  Commissioner of Patents and Trademarks